(12) United States Patent
Xiang et al.

(10) Patent No.: US 11,969,509 B2
(45) Date of Patent: Apr. 30, 2024

(54) ADJUSTABLE EXTERNAL FIXING BRACE

(71) Applicant: Wuhan Xunshu Technology Co., Ltd., Hubei (CN)

(72) Inventors: Guxi Xiang, Hubei (CN); Zhiwei Ouyang, Hubei (CN)

(73) Assignee: Wuhan Xunshu Technology Co., Ltd., Hubei (CN)

( * ) Notice: Subject to any disclaimer, the term of this patent is extended or adjusted under 35 U.S.C. 154(b) by 461 days.

(21) Appl. No.: 16/755,034

(22) PCT Filed: Aug. 22, 2018

(86) PCT No.: PCT/CN2018/101710
§ 371 (c)(1),
(2) Date: Apr. 9, 2020

(87) PCT Pub. No.: WO2019/072026
PCT Pub. Date: Apr. 18, 2019

(65) Prior Publication Data
US 2021/0187153 A1 Jun. 24, 2021

(30) Foreign Application Priority Data
Oct. 12, 2017 (CN) .......................... 201710945969.X

(51) Int. Cl.
*A61L 15/12* (2006.01)
*A61F 5/01* (2006.01)
(Continued)

(52) U.S. Cl.
CPC .......... *A61L 15/125* (2013.01); *A61F 5/0104* (2013.01); *A61F 13/048* (2013.01);
(Continued)

(58) Field of Classification Search
CPC ........ A61L 15/12; A61L 15/125; A61L 15/14; A61L 2400/16; A61F 5/01; A61F 5/0102;
(Continued)

(56) References Cited

U.S. PATENT DOCUMENTS

| 4,473,671 A * | 9/1984 | Green ................ C08G 18/4238 |
| | | 523/105 |
| 2008/0154164 A1* | 6/2008 | Sheehan .................... A61F 5/01 |
| | | 523/105 |

(Continued)

FOREIGN PATENT DOCUMENTS

| CN | 1544096 A | * | 11/2004 | ............. A61L 15/00 |
| CN | 102430156 A | * | 5/2012 | ............. A61L 31/06 |
| WO | WO 2016/142319 A1 | | 9/2016 | |

OTHER PUBLICATIONS

Translation of CN-102430156-A (Year: 2012).*
Translation of CN-1544096-A (Year: 2004).*

*Primary Examiner* — Rachael E Bredefeld
*Assistant Examiner* — Seth R. Brown
(74) *Attorney, Agent, or Firm* — Hammer & Associates, P.C.

(57) ABSTRACT

A medical fixing brace, wherein at least one surface is provided with a plurality of step holes for mounting snap-fit seats and posts; the thickness of the mesh plate is made thinner at the step holes; and each of the step holes is assembled with some parts of the snap-fit seats and posts. According to the invention, the fixing brace can be used for both the left body and the right body, convenient for the doctor; the product does not absorb water and has no pad structure, so it is quick in drying after bathing, and it is good in comfort for the wearer; any pruritus and dermatitis can be avoided; and the external fixing brace according to the (Continued)

invention can be used for bone support of the upper limb, the neck, the chest, the waist, the lower limb and the like.

13 Claims, 4 Drawing Sheets

(51) Int. Cl.
    *A61F 13/00*     (2024.01)
    *A61F 13/04*     (2006.01)
    *A61L 15/14*     (2006.01)
    *B29B 9/06*     (2006.01)
    *B29C 45/00*     (2006.01)
    *B29K 67/00*     (2006.01)
    *B29K 105/16*     (2006.01)
    *B29L 31/00*     (2006.01)

(52) U.S. Cl.
    CPC .............. *A61L 15/12* (2013.01); *B29B 9/06* (2013.01); *B29C 45/0001* (2013.01); *A61F 2013/00489* (2013.01); *A61F 2013/00553* (2013.01); *A61F 2013/00621* (2013.01); *A61L 15/14* (2013.01); *A61L 2400/16* (2013.01); *B29K 2067/00* (2013.01); *B29K 2105/16* (2013.01); *B29K 2995/006* (2013.01); *B29L 2031/753* (2013.01)

(58) Field of Classification Search
    CPC .......... A61F 5/0104; A61F 5/05; A61F 5/058; A61F 13/04; A61F 13/048; B29B 9/06; B29C 45/0001; B29K 2067/00; B29K 2105/16; B29K 2995/006; B29L 2031/753; A44B 17/00; A44B 11/25; A44B 11/2553; A44B 11/2557; A44B 11/2561; A44B 11/2592; A44C 5/20575; A44C 5/20; A44C 5/2066; A43C 11/00; A43C 11/06; A43C 11/12
    USPC ................ 602/5–6, 12, 16; 24/68 SK, 682.1
    See application file for complete search history.

(56) References Cited

U.S. PATENT DOCUMENTS

2015/0033507 A1*   2/2015   Brigato ................ A44B 17/007
                                              24/95
2017/0042715 A1*   2/2017   Park ...................... A61F 5/0104

* cited by examiner

ADJUSTABLE EXTERNAL FIXING BRACE

This PCT application claims priority and its benefit of the Chinese Patent Application No. 201710945969.X filed on Oct. 12, 2017, entitled "Adjustable External Fixing Brace, Composition of the same, Process for Making the same, and Method of Using the same."

FIELD OF THE INVENTION

The present invention relates to an adjustable external fixing brace, in particular to a versatile flexible mesh plate made from a shape memory material, and belongs to the technical field of external fixation for a broken bone.

PRIOR ART

In prior art, polycaprolactone (PCL) is often used as an external fixation material for fracture of human bones. Due to the fact that melting point of polycaprolactone is low, the melt strength is sharply reduced for crystal melting happens near the melting point. Like a limp of cement with high viscosity in its softening process, it is difficult for PCL material to have a formation. Due to the above properties of polycaprolactone, it is more difficult for PCL to be used for preparing such a complex structure as orthopedic brace (or called as support or cast). In particular, it is difficult for PCL to use in any injection molding process. In the prior art, a raw solid plate for bone fixing brace is usually formed using thermoplastic material in a process of molding or calendaring, subsequent processing includes such as shearing/cutting, punching, irradiating the punched raw plate, and spraying anti sticking coating on the punched raw plate. In clinical use, the raw plate needs to be further cut according to a patient's shape of an injured position so as to make his special bone fixing support. Due to the fact that an incision edge of the raw plate is free of anti-sticking coating, adhesion is easy to occur when the special bone fixing support is heated and molded clinically. In addition, in the prior art, the prefabricated holes provided on the versatile plate are uniformly distributed, the holes are too small to change their size and shape according to the needs of different wound position of the patient. Moreover, the holes are too small to facilitate air flowing or bathing on where is braced/supported.

WO2014/084425A1 discloses a shape memory mesh plate, which is made in a process as follows: a raw thermoplastic material is softened, molded or woven into a mesh plate in a smelting machine; then the mesh plate is immersed in an anti-sticking liquid, to make the thermoplastic material completely covered by an anti-sticking coating so as to form a layer of anti-sticking shell. A fixing support can be prepared from the mesh plate during its softening. In such a technology, it takes a long time for molding, and it is with a high production cost.

In a conventional clinical use, the shape memory mesh plate distributed with large ventilation holes is heated to be softened at temperature of 55-80° C., then is stretched and attached to where a patient's bone is injured. Finally, the two sides of the mesh plate are connected with each other by means of an enclosing and locking means. Unfortunately, as a large drawback of the prior art, both the anchoring end and the locking end of the enclosing and locking means cannot be rotatable themselves, as a result, in clinical use, after the mesh plate is stretched, it is difficult for the anchoring end and the locking end of the mesh plate to align completely, making difficult to close the outer fixation brace, or making the adjustability worse.

Especially, in the prior art, as an intermediate of the medical fixing support, one type of mesh plate is made for the left arm, foot or leg, while another type of mesh plate is made for the right arm, foot or leg. The mesh plate for the left arm, foot or leg cannot be used for the right arm, foot or leg, so that the mass for any type of the mesh plate cannot be increased, thus it is difficult to further reduce the cost and make clinical use more convenient.

SUMMARY OF THE INVENTION

An object of the invention is to provide an adjustable fixing support, which is one-time formed in injection molding process for a whole mesh plate, does not need to be cut to fit any specific patient's wounded position, and prevents the mesh plate adhered during use, so that it is simple and quick for a doctor to operate a brace installation in all levels of hospitals.

Another object of the present invention is to provide an adjustable fixing support made from a composite material by means of injection molding, which makes it easy to demold after injection molding resulted from the composite material's new properties, so that the formed mesh plate does not adhere itself in the injection molding process. Therefore, the prior art process (with steps for molding or calendaring for forming a solid raw plate, punching holes on the raw plate, spraying on surfaces of the raw plate so as to have an anti-sticking layer) can be given up. On the other hand, there appears a novel process, in which a homogeneous material is used for directly injection molding of the mesh plate with large air holes and without coating, so that the process is simplified, the production cost is greatly reduced, and comfort feeling of patients is greatly improved.

Thus, the present invention is related to a polycaprolactone composite material, whose formula, with components in parts by weight, is: 40-80 wt % of polycaprolactone, 15-55 wt % of filler, and 5-15 wt % of auxiliary materials. A method for preparing the polycaprolactone composite material comprises the following steps: weighing each of components according to the formula of the polycaprolactone composite material, respectively; mixing the weighed components so as to obtain a mixed material; melt extruding and graining the mixed material so as to obtain the polycaprolactone composite material, wherein the melt extruding is performed in process conditions as follows: temperature of a first zone (rear zone) is 130-140° C., temperature of a second zone (middle zone) is 140-150° C., temperature of a third zone (middle zone) is 150-160° C., temperature of a fourth zone (front zone) is 160-170° C., temperature of an injecting nozzle is 170-180° C., residence time is 1-2 min, and pressure is 10-20 MPa; or, temperature of a first zone is 60-130° C., temperature of a second zone is 130-200° C., temperature of a third zone is 150-210° C., temperature of a fourth zone is 160-220° C., temperature of an injecting nozzle is 170-200° C., residence time is 1-5 min, and pressure is 10-100 MPa.

The polycaprolactone composite material contains polycaprolactone as a matrix material, as well as filler and lubricant agent for modification of the composite material. The components are synergistic in the melt extrusion process, and the blends react with polycaprolactone molecules to form covalent bonds, so that the interface compatibility between polycaprolactone and other components is improved, and the polycaprolactone composite material is endowed with excellent mechanical properties and anti-sticking performance. According to the method for preparing the polycaprolactone composite material, the raw material can be obtained by mixing all the components according to a formula, then performing a melt extrusion at the appropriate temperature. The preparation method is simple in process, easy to control in condition, low in cost and low in required equipment, so it is suitable for industrial production.

To this end, in accordance with the first aspect of the present invention, there is provided an adjustable external fixation brace, characterized in that the outer fixation brace is one-time formed by an injection molding process (on the other hand, in the prior art, the outer fixation brace is molded or calendered into a solid plate, followed by cutting to raw products, perforating on each raw product, the spraying antibonding agent on surfaces of each raw product), so as to form a shape memory mesh plate distributed with large ventilation holes (in the prior art, however, the ventilation holes are regular small holes); and the raw material of the mesh plate is doped with an anti-sticking agent.

Preferably, the ventilation holes (openings for air flowing) are macropores (large size holes) which have at least one of the following features: a hole having an arc transition; a span of at least greater than the thickness of the mesh plate (preferably less than 50 times of the thickness, more preferably less than 30 times of the thickness); a ratio of maximum span to minimum span is 1:1 to 40:1 (preferably 1:1 to 30:1, more preferably 1:1 to 20:1); the minimum transition radius is 10 degrees; the minimum transition radius is 0.5 mm; the width of any rib between two large openings is at least greater than the thickness of the mesh plate (preferably greater than 1.5 times of the thickness, more preferably greater than 2 times of the thickness); and a sum of the areas (breathable area) occupied by the ventilation holes is 7-70%, preferably 20-70%, more preferably 29-60%, and most preferably 30-55% of the total area of the external fixing brace (i.e. a case or a support).

Preferably, the shape memory mesh plate has at least one of the following features: a thickness of at least 1.5 mm (preferably 4-6 or 4-8 mm, more preferably 5 mm); a thickness for a special portion (contacting a certain joint or bony protrusion in use) of the mesh plate is made thinner; and in a special area, there is arranged a hole (as a circular, oval-shaped, generally triangular, peach-shaped, etc.) pre-arranged for the thumb, etc.

Preferably, the anti-sticking agent may be a single or composite anti-adhesive that prevents the shape memory mesh plate from sticking during injection molding to facilitate removal from the mold.

Preferably, the adjustable external fixation brace is used for, but not limited to, a patient's injured position requiring rehabilitation as follows: hand, upper limb, lower limb, neck, chest, waist, or foot.

Preferably, adjacent the two sides, parallel to the longitudinal direction, of the adjustable outer fixing support are provided with a snap-fit means of the enclosing and locking means, which can be bonded on, inserted into, or integrated with the shape memory mesh plate; the thickness of the snap-fit means can be substantially the same as that of the shape memory mesh plate; and the enclosing and locking means can be a backstop buckle structure, a nylon buckle belt structure, a button structure, a tenon structure, or a waistband structure with combination of a fixing needle and a hole.

According to the second aspect of the present invention, there is provided an adjustable external fixation brace, characterized in that it is made from a modified high molecular material, comprising an anti-sticking agent selected from the group consisting of polycaprolactone, polypropylene, polyethylene, calcium carbonate, glass fibers, monoalkoxy titanate coupling agents, graft polypropylene, graft polyethylene, polyethylene wax, calcium stearate, stearamide, vegetable oil, the blends thereof, and the combinations thereof.

In accordance with the third aspect of the present invention, there is provided a process for making an adjustable external fixing support, characterized in that the process comprises the following steps: injection molding a blend containing an anti-sticking agent and components selected from the group consisting of polycaprolactone, polypropylene, polyethylene, calcium carbonate, glass fiber, monoalkoxy titanate coupling agent, grafted polypropylene, grafted polyethylene, polyethylene wax, calcium stearate, stearic amide, vegetable oil, and combination thereof; and one-time forming a shape memory mesh plate with large air holes.

In accordance with the fourth aspect of the present invention, there is provided a method for using an adjustable external fixation brace, characterized in that heating at 70-80° C. so as to soften a shape memory mesh plate, which is made from a modified high molecular material, and is distributed with large openings; directly contacting the shape memory mesh plate on the patient's injured position, or stretching the shape memory mesh plate to a proper size according to requirements, and surrounding it around the patient's wounded position; closing the cleavage between the two sides of the shape memory mesh plate by means of the enclosing and locking means; and cooling the shaped mesh plate to temperature below 60° C., thus self-hardening the shaped mesh plate, setting the shaped mesh plate, making the shaped mesh plate formed, making the shaped mesh plate subjected to hold any weight, so as to function the shaped mesh plate as an external fixing brace.

According to the fifth aspect of the present invention, there is provided an adjustable external fixation brace, characterized in that it is a plate with large through holes. According to the design, it is facilitated to directly inspect wound recovering progress, and prevent from occurring complications after trauma. It is the large through holes arranged on the mesh plate that make the skin in the injured position good for air flows and quick-drying after taking a shower, so as to improve the health condition of the patient's skin at the injured position, prevent pruritus, and avoid occurrence of dermatitis. And by prearranging the big holes of the mesh plate, it makes the brace light in weight.

In accordance with the sixth aspect of the present invention, there is provided an adjustable external fixation brace, characterized in that the fixing brace is always matched with the enclosing and locking means which are adjustable and easy to be disassembled. In this case, in the whole recovering course, a clamping tightness of the brace can be adjusted at any time according to swelling condition where the patient is wounded, so that suitable compression on the corresponding soft tissue is maintained, so as to keep a very good fixing effect of the brace.

According to the invention, the thermoplastic memory material is adopted, its tensile property is good, any angle and deformation in any direction can be generated, and in particular, the net like structure has better stretchability. In this case, one type of the mesh plate can be extensively used for different patients, fat or thin. Therefore, types of the mesh plate are reduced, production cost for any type of the mesh plate is reduced, and the purchased number of types of the mesh plate by any hospital is also reduced.

According to the invention, the mesh plate with large size holes made by the one-time injection molding process does not have any punching process, so no waste and leftover materials are generated, and no coating procedure is needed. In this case, without additional coating, any adhesion is avoided, so the production efficiency is high, and the manufacturing cost is low.

According to the invention, the mesh plate is an intermediate of the fixing support which is made from a thermoplastic material with good processing performance (suitable for injection molding), certain ductility and non-adhesion, and which is injected and molded into products for different human body portions (hands, limbs, neck, chest, waist or feet).

According to the present invention, the mesh plate has arranged some large size holes that facilitate enjoy fresh air; the mesh plate consists of a single piece or multiple pieces; the mesh plate has different enclosing and locking means; a pattern and thickness on a special portion of the mesh plate can be different to other portions of the mesh plate, e.g. thickness of the mesh plate corresponding to ulnar stem, talar, etc. is less than or equal to the thickness of other portions of the mesh plate; and so on.

According to the invention, the mesh plate can be stretched or deformed in any way to correspond to the injured position of the human body fracture, so as to obtain an external fixing brace with different shapes or different spatial orientations. No cropping is required at the two sides of the mesh plate. The mesh plate cannot stick one portion to another in use. The mesh plate is made from the same chemical material, except the enclosing and locking means, and the surface of the mesh plate does not need to be coated or impregnated with other substances. After being enclosed by the enclosing and locking means, a fixing brace with an irregular barrel shape suitable for the external shape of the wounded limb portion of the human body can be formed. The mesh plate can be used to fix all possible positions of human body, such as neck, chest, limbs, etc. The fastening tightness of the fixing brace can be adjusted at will according to the swelling change at the affected position with respect to the fracture. It is convenient to disassemble the fixing brace, so that the external injury treatment and nursing of the affected position are facilitated. The material of the mesh plate does not absorb water, so the fixing brace can wear even in bathing.

The invention overcomes the prejudice of the traditional technology, has no respect to the traditional process, is not limited by the traditional material selection, but instead opens the innovation, selects a new material, a new technology, a new style and a new structure, provides a rehabilitation support which is lower in manufacturing cost, simpler in manufacturing process, more convenient for doctors to use, safer and more comfortable to wear by patients, and more suitable for fracture fixation according to the anatomy of a human body.

According to the invention, at the anchoring end and the locking end of the enclosing and locking means, the pins or posts themselves can be freely rotated to facilitate the clinical use. Regardless of how the mesh plates are stretched, the corresponding anchoring end and the locking end can be completely aligned with each other through adaptive steering adjustment, so that the enclosing of the external fixing support becomes easy, and its adjustability is excellent.

According to the invention, as an intermediate product for forming the medical fixing support, it is no longer to separately prepare the mesh plate used for the left arm, foot or leg and that used for the right arm, foot or leg, so that a versatile mesh plate is formed and can be used both for the left arm and the right arm, both for the left foot or leg and for the right foot or leg, therefore a batch of any type of the mesh plate can be improved, the cost for making the mesh plate is further reduced, and clinical use of the mesh plate is facilitated.

DETAILED DESCRIPTION OF THE PREFERRED EMBODIMENTS

Figure 1:
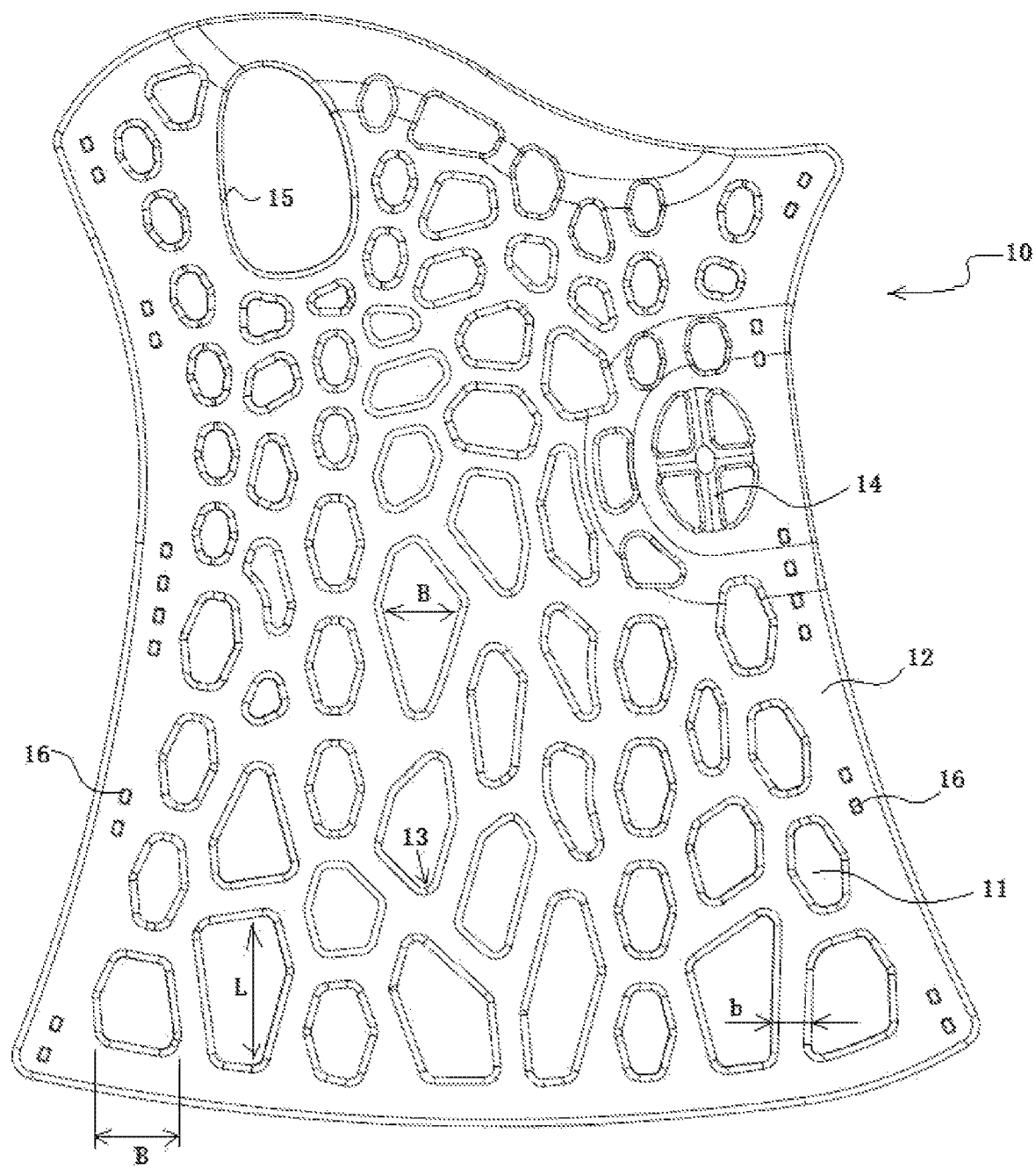
FIG. 1 is a schematic view of an adjustable external fixation brace in an intermediate state in accordance with one embodiment of the present invention.

The invention provides a thermoplastic material capable of injection molding a complex structural medical brace (support or cast), wherein the thermoplastic material has low-temperature thermoplastic properties, is of ductility, and is free of any adhesion during clinical use. According to some embodiments of the present invention, the thermoplastic material comprises: a main material such as polycaprolactone; an auxiliary material such as polyethylene or polypropylene; a coupling agent such as an oxytitanate coupling agent; a grafting agent such as graft polypropylene or graft polyethylene; and a lubricant such as polyethylene wax, calcium stearate, stearamide or vegetable oil.

In order to more clearly understand the technical problems, technical solutions, and beneficial effects to be solved by the present invention, a more detailed description of the invention will be made as follows, taken in conjunction with the accompanying drawings. It should be understood that the specific embodiments described herein are merely illustrative of the invention and are not intended to limit the invention. According to the embodiment of the invention, a polycaprolactone composite material with good interface compatibility and excellent mechanical properties between polycaprolactone and fibers is provided. The polycaprolactone composite material comprises components in percentage by weight as the following formula: 40-80 wt % of polycaprolactone, 15-55 wt % of filler, and 5-15 wt % of auxiliary materials.

In particular, the polycaprolactone is a matrix component. In their melt extrusion process, the molecules of the polycaprolactone and other components, especially lubricant, are synergistic, so that the interface problem between the polycaprolactone and the filler is improved, and the mechanical properties of the polycaprolactone composite material are endowed. To further exhibit an interfacial compatibility between the polycaprolactone and the filler, a further detailed description of the invention will be made with respect to the formulation and preparation method of the examples of the polycaprolactone composite.

Molding Time:
Injection molding is performed with polycaprolactone composite in Color Plate Injection Molding Plant.
Equipment Model: SSF 380-III,
Parameters: Nozzle Temperature=160° C.;
First Segment Temperature=160° C.;
Second Segment Temperature=160° C.
Time for normally completing formation: counted in case of spraying a release agent.

TABLE 1

Content (wt %) of components in some embodiments of the present invention.

| Component\Example No.: | 1 | 2 | 3 | 4 | 5 | 6 | 7 | 8 | 9 | 10 | 11 | 12 |
|---|---|---|---|---|---|---|---|---|---|---|---|---|
| Polycaprolactone | 40 | 40 | 40 | 40 | 45 | 45 | 50 | 50 | 50 | 50 | 55 | 55 |
| Polypropylene | 48 |  | 4 |  | 35 | 25 | 25 |  | 25 |  | 23 |  |
| Polyethylene |  | 50 | 44 | 50 | 10 | 20 |  | 15 |  | 15 |  | 23 |
| Calcium Carbonate |  |  |  |  |  |  |  | 15 | 15 | 15 | 4 | 5 |
| Glass Fiber |  |  |  |  |  |  | 15 | 8 |  | 8 | 10 | 10 |
| Monoalkoxy Titanate Coupling Agent | 1 | 1 | 1 | 1 |  |  |  | 1 |  | 1 | 1 |  |
| Grafted Polypropylene | 4 |  | 4 |  | 1.5 | 1.5 | 4 |  | 4 |  |  |  |
| Grafted Polyethylene |  | 2 |  | 2 | 1.5 | 1.5 |  | 2 |  | 2 | 2 | 2 |
| Polyethylene Wax | 7 |  | 7 |  |  |  |  | 4 |  | 4 | 2 | 2 |
| Calcium stearate |  | 7 |  | 7 |  |  |  | 2 | 5 | 2 | 2 |  |
| Stearamide |  |  |  |  | 7 | 7 |  | 3 |  | 3 |  | 2 |
| Vegetable Oil |  |  |  |  |  |  | 6 |  | 1 |  | 1 | 1 |

| Component\Example No.: | 13 | 14 | 15 | 16 | 17 | 18 | 19 | 20 | 21 | 22 | 23 | 24 |
|---|---|---|---|---|---|---|---|---|---|---|---|---|
| Polycaprolactone | 55 | 55 | 60 | 60 | 60 | 60 | 65 | 65 | 65 | 65 | 70 | 70 |
| Polypropylene | 23 |  |  | 15 |  | 15 | 10 |  | 10 |  |  |  |
| Polyethylene |  | 23 | 20 |  | 20 |  |  | 15 |  | 15 | 10 | 10 |
| Calcium Carbonate | 10 | 10 | 3 | 3 | 9 | 15 | 8 | 5 | 10 | 6 | 2 | 10 |
| Glass Fiber | 4 | 5 | 9 | 15 | 3 | 3 | 10 | 5 | 8 | 5 | 10 | 2 |
| Monoalkoxy Titanate Coupling Agent | 1 |  | 1 |  | 1 |  |  |  |  |  |  |  |
| Grafted Polypropylene |  |  |  | 3 |  | 3 | 2 |  | 2 |  |  |  |
| Grafted Polyethylene | 2 | 2 | 2 |  | 2 |  |  | 3 |  | 3 | 3 | 3 |
| Polyethylene Wax | 2 | 2 |  | 3 | 1.5 | 1.5 |  | 2.5 | 2 | 2 | 2 |  |
| Calcium stearate | 2 |  | 3 | 1 | 2.5 | 1.5 | 3 | 1.5 | 3 |  |  |  |
| Stearamide |  | 2 | 1 |  | 0.5 | 0.5 | 3 | 4 | 0.5 | 0.5 |  | 2 |
| Vegetable Oil | 1 | 1 | 1 |  | 0.5 | 0.5 | 2 |  | 0.5 | 0.5 | 3 | 1 |

Performance Tests:
Samples of the polycaprolactone composite material prepared in Examples 1-24 above are tested for related performance using the ASTM D-790 test standard.
Where test method each related property for is as follows:
Elongation at Break:
Samples of the tested material: pressed into Type I;
Spline Size (mm): Length×End Width×Thickness= (150±3)×(10±0.3)×(4±0.3);
Tensile Speed: 50 mm/min.

Flexural Strength and Flexural Modulus:

Test standard: ASTM D-790;
Length×End Width×Thickness=(150±3)×(10±0.3)×(3±0.3);
Bending speed: 20 mm/min.

The test results of the related performances of the polycaprolactone composite samples prepared in Examples 1-24 above are shown in Table 2, respectively.

TABLE 2

Test Results According to Some Embodiments of the Invention

| Component\Example No.: | 1 | 2 | 3 | 4 | 5 | 6 | 7 | 8 | 9 | 10 | 11 | 12 |
|---|---|---|---|---|---|---|---|---|---|---|---|---|
| Elongation at Break (%) | 1.5 | 1.5 | 1.5 | 1.5 | 1.7 | 1.7 | 1.8 | 1.8 | 1.8 | 1.8 | 2.1 | 2 |
| Molding Time (s) | 120 | 120 | 120 | 120 | 130 | 130 | 140 | 140 | 140 | 140 | 160 | 160 |
| Flexural Strength (MPa) | 115 | 115 | 115 | 115 | 110 | 110 | 110 | 110 | 110 | 110 | 104 | 105 |
| Flexural Modulus (MPa) | 4100 | 4150 | 4100 | 4103 | 3820 | 3800 | 3515 | 3510 | 3515 | 3510 | 3340 | 3345 |

| Component/Example No.: | 13 | 14 | 15 | 16 | 17 | 18 | 19 | 20 | 21 | 22 | 23 | 24 |
|---|---|---|---|---|---|---|---|---|---|---|---|---|
| Elongation at Break (%): | 2.1 | 2 | 2.2 | 2.3 | 2.2 | 2.2 | 2.3 | 2.3 | 2.3 | 2.3 | 2.5 | 2.5 |
| Molding Time (s) | 160 | 160 | 180 | 180 | 180 | 180 | 200 | 200 | 200 | 200 | 230 | 230 |
| Flexural Strength (MPa) | 104 | 105 | 101 | 100 | 101 | 100 | 95 | 96 | 95 | 96 | 94 | 94 |
| Flexural Modulus (MPa) | 3340 | 3345 | 3230 | 3256 | 3230 | 3256 | 3010 | 3015 | 3010 | 3015 | 2890 | 2890 |

From the above examples, through modification of polycaprolactone composite material, it can be seen that the mechanical property and the anti-sticking property of the polycaprolactone composite samples are effectively improved. The above samples are only preferred embodiments of the invention, but do not limit the invention. Any modification, equivalent replacement and improvement made in the invention and principles shall be included in the scope of protection of the invention.

Test methods and related parameters can also be as follows:

Elongation at Break:
   Test standard: GB 1040-92;
   The samples: pressed into an I-shaped;
   Spline size (mm):
      length=156±3;
      end width=20±0.2;
      intermediate parallel length=60±0.5;
      intermediate parallel width=10±0.2; and
      thickness=4±0.2;
   Stretching speed: 50 mm/min.

Tensile Strength:
   Test standard: ASTM D-638;
   The samples: type I;
   Spline size (mm):
      Length×End Width×Thickness=(176±2)×(12.6±0.2)×(3.05±0.2);
   Stretching speed: 50 mm/min±10%.

Flexural Strength and Flexural Modulus:
   Test standard: ASTM D-790;
   Sample size (mm):
      length=127±1;
      width=12.7±0.2;
      thickness=3.2±0.2;
   Bending speed: 20 mm/min.

Molding Time:
   Injection molding is performed with polycaprolactone composite in Color Plate Injection Molding Plant.
   Equipment Model: SSF 380-III,
   Parameters: Nozzle Temperature=160° C.;
      First Segment Temperature=160° C.;
      Second Segment Temperature=160° C.
   Time for normally completing formation is counted in case of spraying a release agent.

According to the test result, a medical fixing support with complex structure can be manufactured through injection molding by adopting the composite material formula provided by the invention. Especially, according to the present invention, the process for one time product formation is simple, the production cycle is short, the production cost is low, the clinical use is simple, any further cutting the product to meet usage of any specific patient is avoided, the clinical patient comfort feeling for wearing the product is greatly improved, and adhesion during heating and shaping operation in clinical use is prevented.

According to the present invention, by blending with some fillers, the raw material to make medical fixing support becomes to have better processing and forming performance, making possible to form a complex structure by performing an injection molding process. And the prepared product has certain ductility and is free of adhesion during clinical use.

The invention does not use any traditional process, nor is limited by traditional material selections, but selects a new material, a new process, a new pattern and a new structure, so that the manufacturing cost becomes lower, and the manufacturing process becomes simpler. In addition, it is more convenient for doctors to use the invented product, and it is safer for patients to wear the invented product, and it is more suitable for the fixing support for broken bone rehabilitation to be placed on the fracture position following the anatomy of the human body.

Figure 2A:
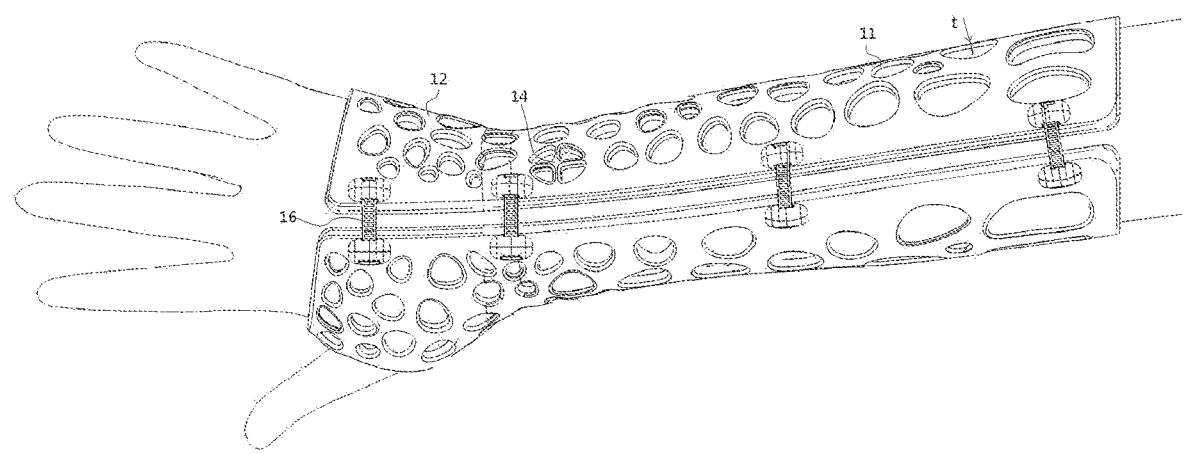
FIGS. 2a-2b are schematic views of an adjustable external fixation brace in a broken bone supporting state of the embodiment as shown in FIG. 1.
Figure 2B:
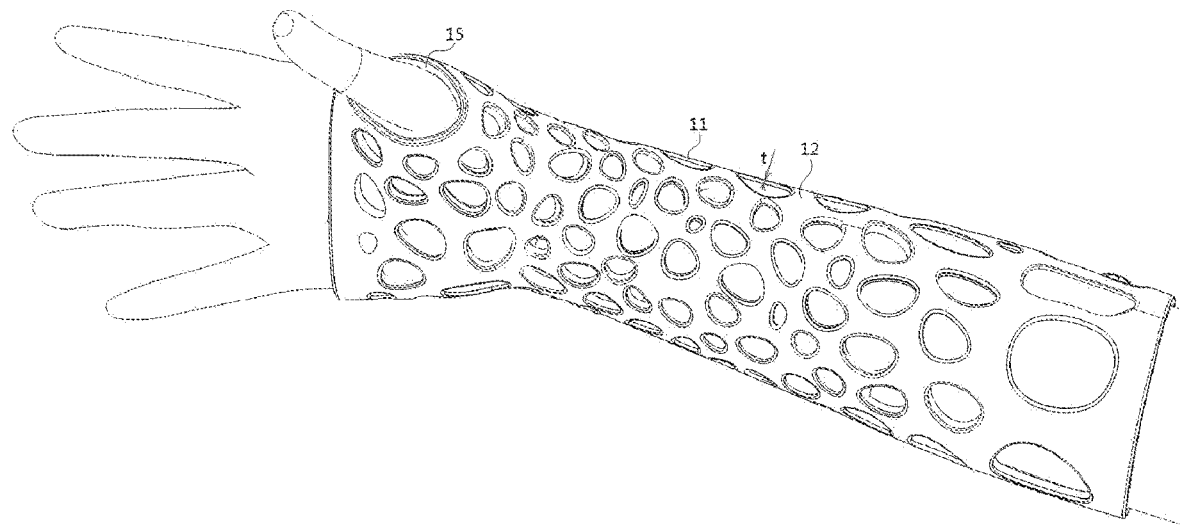

FIG. 1 is a structural view of an adjustable external fixation brace in an intermediate state in accordance with one embodiment of the present invention. FIG. 2a is a structural view of the embodiment in usage status as shown in FIG. 1. FIG. 2b is another structural view of the embodiment in usage state as shown in FIG. 1.

FIG. 1 shows a raw product of brace/support 10 for adjustably enclosing and fixing on a position of a broken bone externally. Its raw material contains an anti-sticking agent. A shape memory mesh plate 12, or an intermediate of the brace 10, is formed one-time by a molding process, having a series of different shaped large openings 11 fully distributed on the mesh plate 12. This is completely different from prior art. In prior art, a method for producing a mesh plate comprises the steps as follows: forming a solid plate through a vulcanization process; applying an anti-sticking agent on surfaces of the solid plate; punching through holes on the solid plate; then cutting edges of the plate to obtain the needed shape plate. Moreover, in the lag prior art, only a regular array of small holes can be formed, large openings (especially random-shaped large openings) cannot be formed. Random shaped large openings are conducive to obtain isotropy of the formed mesh plate, so that the structural strength of the shape memory mesh plate 12 can be ensured by any stretching deformation of the shape memory mesh plate 12 in any direction. The regular array of large openings instead of small holes in the prior art does not maintain good isotropy, i.e., it is possible to destroy the intermediate of the medical fixing brace by stretching the mesh plate in certain directions.

As shown in FIGS. 1-2, the irregular shaped large hole or opening 11 has a transition arc 13 whose minimum transition radius is 0.5 mm and minimum transition fillet is 10 degrees.

Span B is at least greater than thickness t, preferably less than 50 times of the thickness, and more preferably less than 30 times of the thickness.

The ratio of maximum span L to minimum span B is 1:1 to 40:1, preferably 1:1 to 30:1, and more preferably 1:1 to 20:1.

The width b of any rib between two adjacent large openings 11 is at least greater than the thickness of the mesh plate, preferably greater than 1.5 times of the thickness, and more preferably greater than 2 times of the thickness.

The sum of the areas occupied by the large openings 11 is 25-98%, preferably 27-80%, more preferably 29-60%, and most preferably 30-55% of the full area of the shape memory mesh plate 12.

The shape memory mesh plate 12 has a thickness of at least 3 mm, preferably 4-6 mm, and more preferably 5 mm. For example, the thickness of the portion 14 contacting to the wrist bone in use is thinner than the other portions; and a particular shaped oval hole 15 corresponding to the thumb is pre-arranged on a suitable portion of the mesh plate. The oval hole 15 may be in a shape of a peach, ellipse, generally triangular, etc. depending on actual needs.

The anti-sticking agent may be a single or composite anti-adhesive that prevents the shape-memory mesh plate 12 from sticking during the molding process to facilitate removal from the mold.

As shown in FIG. 1, the adjustable external fixing brace 10 is used for rehabilitation of a patient's arm. In other embodiments, the concepts of the present invention are equally applicable to a brace for fixing on a position of limbs, chest, neck, waist, hand, foot, etc. where has a broken bone.

Adjacent to the two sides, parallel to longitudinal direction, of the adjustable outer fixing support 10 are provided with a plurality of snap-fit means of the enclosing and locking means 16, which may be adhered to, inserted into, or integral with the shape-memory mesh plate 12. The thickness of snap-fit means of the enclosing and locking means 16 may be substantially the same as that of the shape-memory mesh plate 12.

Figure 3A:
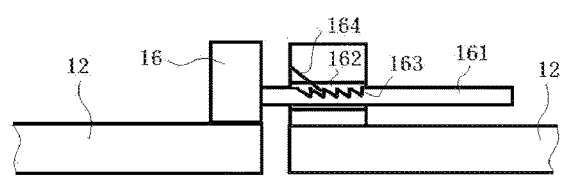
FIGS. 3a-3e are schematic views of several kinds of enclosing and locking means of the adjustable external fixation brace according to embodiments of the present invention.

In the embodiment as shown in FIG. 3a, the enclosing and locking means 16 may be a snap-in configuration. The enclosing and locking means 16 mounted on one side of the shape-memory mesh plate 12 has a check strap 161. There are provided with straight teeth 163 on the check strap 161. The enclosing and locking means 16, which is mounted on the other side of the shape memory mesh plate 12, is provided with a slot 162 and a check rod 164. The slot 162 is provided to make the check strap 161 pass through thereof and make the rod 164 engagement with one of the straight teeth 163, so that the check strap 161 cannot be pulled back to facilitate locking of the enclosing and locking means 16. However, when the rod 164 is manually turned away, the check strap 161 can freely drawback to facilitate relaxation of the enclosing and locking means 16.

Figure 3B:
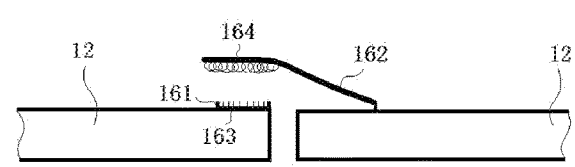

In the embodiment as shown in FIG. 3b, the enclosing and locking means 16 may be a nylon tape structure. The enclosing and locking means 16 mounted on one side of the shape memory mesh plate 12 is provided with a nylon seat 161 having nylon upright piles 163 thereon. The enclosing and locking means 16, which is mounted on the other side of the shape memory mesh plate 12, is provided with a nylon strap 162 provided with nylon loops 164. If making the nylon upright piles 163 and the nylon loops 164 bond together, the enclosing and locking means 16 is locked. When the nylon loops 164 are manually pulled apart from the nylon upright piles 163, the enclosing and locking means 16 is released.

Figure 3C:
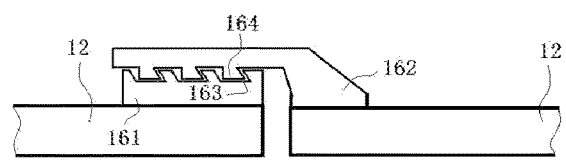

In the embodiment as shown in FIG. 3c, the enclosing and locking means 16 may be a button structure. The enclosing and locking means 16 mounted on one side of the shape memory mesh plate 12 is provided with a button seat 161 having barbed teeth 163 thereon. The enclosing and locking means 16, which is mounted on the other side of the shape memory mesh plate 12, is provided with a button 162 on which hooks 164 are provided. When the hooks 164 are snapped onto the teeth 163, the connection device 16 is locked. When the button 162 is pulled apart manually from the button seat 161, the enclosing and locking means 16 is released.

Figure 3D:
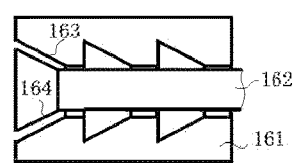

In the embodiment as shown in FIG. 3d, the enclosing and locking means 16 may be a tongue-and-tenon structure. The enclosing and locking means 16 mounted on one side of the shape-memory mesh plate 12 is provided with a female connector 161 having a plurality of stepped grooves 163 in a row. The enclosing and locking means 16, which is mounted on the other side of the shape memory mesh plate 12, is provided with a male connector 162 with a trapezoidal head 164. When the trapezoidal head 164 is inserted into one of stepped grooves 163, the enclosing and locking means 16 is locked. When the trapezoidal head 164 is manually loosened, the enclosing and locking means 16 is also released.

Figure 3E:
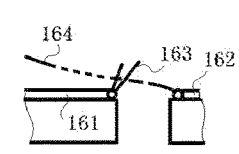

In the embodiment as shown in FIG. 3e, the enclosing and locking means 16 may be a belt with a fixing pin and a series of holes. The enclosing and locking means 16 mounted on one side of the shape-memory mesh plate 12 is provided with a belt fixing end 161 with a fixing needle 163 thereon. The enclosing and locking means 16, which is mounted on the other side of the shape memory mesh plate 12, is provided with a needle receiving end 162 of the belt which is provided with a series of holes 164. When the fixing needle 163 is inserted into one of holes 164, the enclosing and locking means 16 is locked. When manually taking the fixing needle 163 out of the certain hole 164. the enclosing and locking means 16 is released.

According to the invention, the adjustable external fixing support is made from a modified high-molecular material which is selected from the group consisting of polycaprolactone, polypropylene/polyethylene, calcium carbonate, glass fiber, oxytitanate coupling agent, grafted polypropylene, grafted polyethylene, polyethylene wax, calcium stearate, stearamide, vegetable oil, a blend thereof, or a combination thereof.

According to the invention, the adjustable external fixing support is made by the injection molding process, in which the shape memory mesh plate with the large openings distributed thereon is formed in a mold at one time. The molding raw material itself contains the anti-sticking agent, so that the product no longer needs to be coated with the anti-sticking agent on surfaces thereof. In addition, the raw material is selected from the group consisting of polycaprolactone, polypropylene/polyethylene, calcium carbonate, fiberglass, oxytitanate coupling agent, graft polypropylene, graft polyethylene, polyethylene wax, calcium stearate, stearamide, vegetable oil, blends thereof, or combinations thereof.

According to the invention, when the adjustable external fixing support is used by a doctor, firstly, a shape memory mesh plate, which is distributed with large openings and made from a modified high-molecular material, is heated to soften at the temperature of 70-80° C. (or 60-70° C. for softening); then temperature of the shape memory mesh plate distributed with large openings thereon is cooled to 65° C. (preferably less than 60° C., more preferably less than 50° C.) within 15 minutes (preferably 12 minutes, more preferably 10 minutes), then the doctor can encompass the mesh plate on the wounded site where the patient needs to be fixed, with stretching and deforming to make the shape memory mesh plate with distributed large openings fitted to where the patient is injured; then the two cross edges of the shape memory mesh plate distributed with large openings are connected together.

The adjustable external fixation brace according to the present invention employs a thermoplastic memory and degradable material selected from the group consisting of polycaprolactone, polypropylene/polyethylene, calcium carbonate, glass fibers, oxytitanate coupling agents, graft polypropylene, graft polyethylene, polyethylene wax, calcium stearate, stearamide, vegetable oil, blends thereof, and combinations thereof. The mixed raw materials are subjected to injection molding, so that a shape memory mesh plate with large-holes is formed at one time. Preferably, a curing agent, a rigid reinforcing agent and the like are also added into the mixed raw material.

Figure 4:
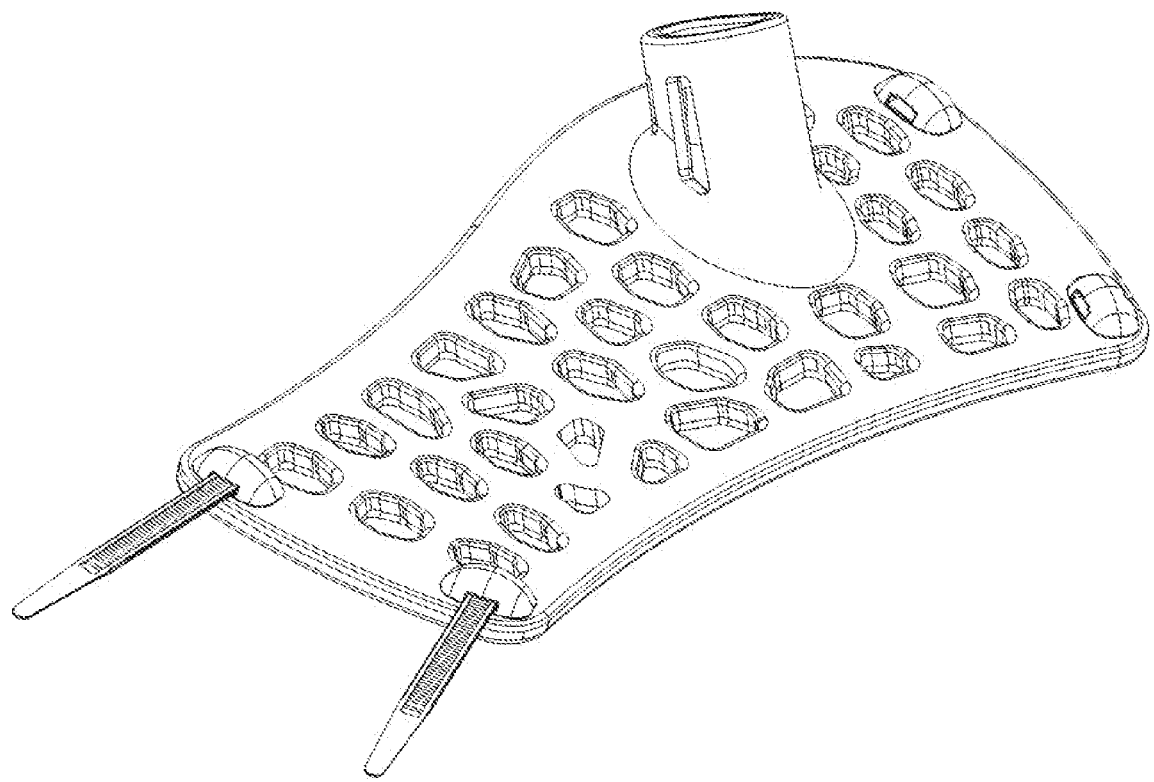
FIG. 4 is a wrist fixing brace, a variation of the arm fixing brace as shown in FIGS. 1-3.

FIG. 4 shows a wrist fixation brace having a structure very similar to the arm fixing support as shown in FIGS. 1-3, and any illustration will not be repeated hereafter.

The invention relates to a support for fixing a position of an injured bone. The support is made by an injection molding. The fixing support is made from a homogeneous shape memory modified material, so it is stretchable and can be deformed to have a spatial curved surface. The fixing support has no coating. The modified material comprises the following components in percentage by weight: 40 to 80% of polycaprolactone, 15 to 55% of filler, and 2.6 to 14.5% of auxiliary materials. As an intermediate of the fixing support, a mesh plate according to the invention is arranged with large air holes, and hollowed-out areas account for 7-70% of the total area of the mesh plate. Recovering of the wound can be inspected directly though the large-holes, so any complication after trauma can be avoided. The enclosing and locking means according to the invention is adjustable, so that the clamping tightness of the fixing brace can be adjusted at any time in the wound recovering period, to enjoy both maintenance of suitable compression on soft tissue and good fixing effect. It is convenient for the doctor to take care of the postoperative wound for the enclosing and locking means is easy to disassemble. During wearing the fixing brace, it is necessary to further modify the formed mesh plate according to a current size of position of the broken bone of the patient, so it is simple and convenient for the doctor to take the shape changed mesh plate as the updated fixing brace. The material according to the invention does not absorb water and has no pad structure, so it is quick in drying after bathing, and it is good in comfort for the wearer. As a result, the health of skin is greatly improved for the skin of the wounded site can enjoy fresh air and even bathing, and any pruritus and dermatitis can be avoided. The external fixing brace according to the invention can be used for bone support of the upper limb, the neck, the chest, the waist, the lower limb and the like.

Figure 5:
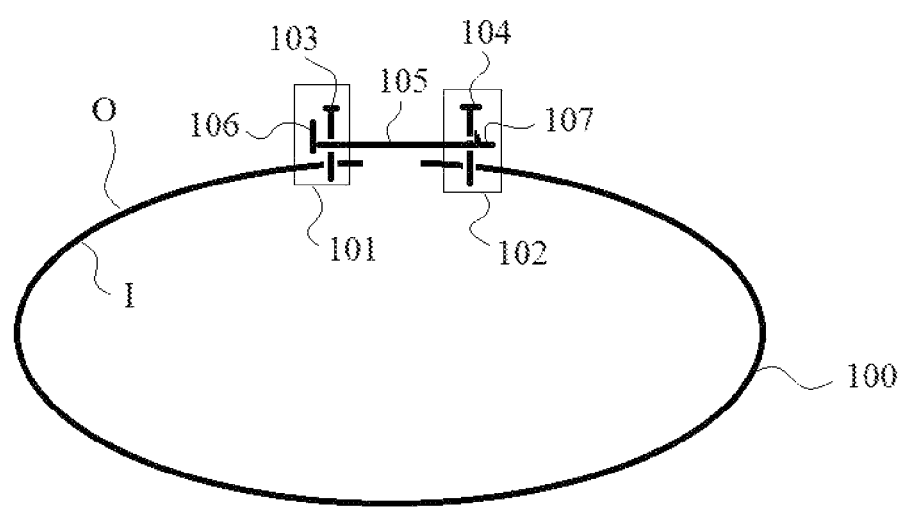
FIG. 5 is a schematic view of the enclosing and locking means of an adjustable external fixing brace in accordance with an embodiment of the present invention.

In the embodiment as shown in FIG. 5, snap-fit means 101, 102 are mounted on both sides of the mesh plate 100 adjacent its lateral edges, respectively. The snap-fit means 101, 102 are each provided with an anchoring end head 103 and a fixing end head 104, respectively, that can be rotatable with respect to the connecting band 105 of the mesh plate 100. In clinical use, the mesh plate 100 is shaped such that its inner surface I surrounds the patient's injury. And on the outer surface O, the anchor end 106 of the connecting band 105 is fixed within the anchoring end head 103, and the fixing end 107 of the connecting band 105 is fixed within the connecting end head 104, thereby enclosing the mesh plate 100.

Figure 6:
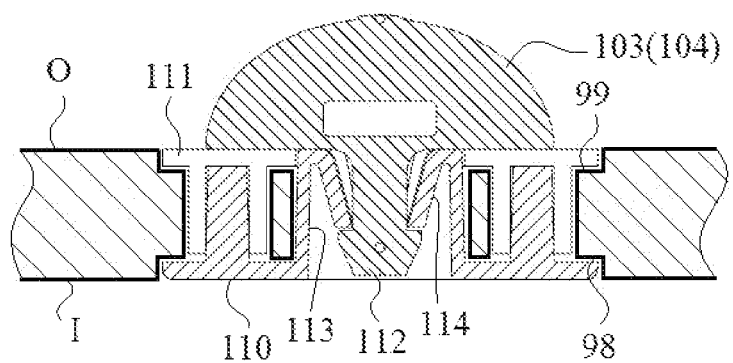
FIG. 6 is a schematic view of the assembled structure of the enclosing and locking means as shown in FIG. 5.
Figure 7A:
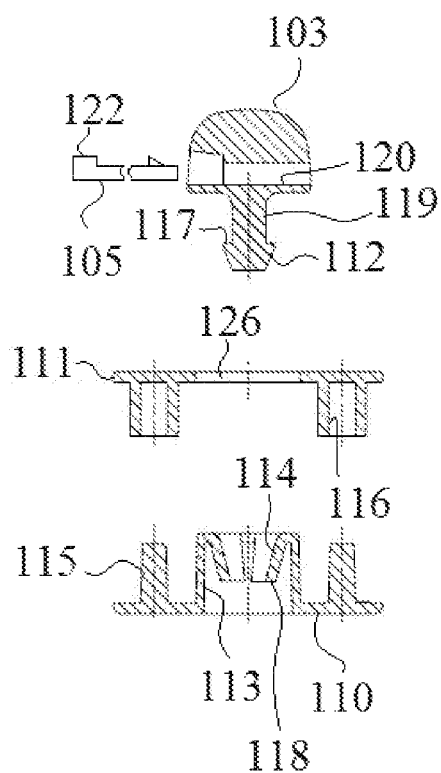
FIG. 7A is a schematic view of the disassembled structure of the anchoring end of the enclosing and locking means as shown in FIG. 6.
Figure 7B:
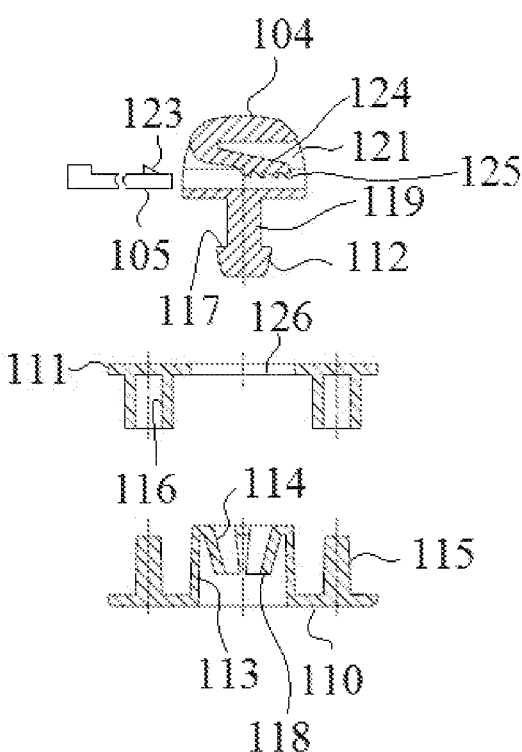
FIG. 7B is a schematic view of the disassembled structure of the locking end of the enclosing and locking means as shown in FIG. 6.

FIG. 6 is a partially enlarged schematic view of a finally positioned and assembled structure of the snap-fit means 101, 102. And FIGS. 7A-7B are schematic exploded views of the positioning and mounting structure of the snap-fit means 101, 102.

As shown in FIGS. 5-6, 7A and 7B, according to the first aspect of the present invention, there is provided a medical fixation brace, which is reshaped from a mesh plate 100 provided with a plurality of large vents, and it is injection molded from a shape memory material; on the front and back surfaces O, I, a plurality of step holes 99, 98 for mounting the snap-fit means 101, 102 are symmetrically arranged along each side of the mesh plate 100 adjacent to its lateral edge, or a plurality of step holes 99, 98 for mounting the snap-fit means are provided on at least one surface thereof; at the step holes 99, 98, the thickness of the mesh plate 100 is thinned; and the step holes 99, 98 are assembled with parts 111, 110 for mounting the end heads.

Preferably, the snap-fit means 101, 102 is provided with a snap-fit seat 110 and a snap-fit post 119; the snap-fit seat 110 is disposed within the mounting pocket/step hole 98 provided on one side I of the mesh plate 100, and the snap-fit post 119 is rotatably inserted into the snap-fit seat 110 from the outer surface O of the mesh plate 100, and cannot be drawn out of the snap-fit seat 110.

Preferably, the snap-fit seat 110 is provided with an elastically expandable check barrel 114. The snap-fit post 119 is provided with a check head 112 with a stop face 117. The resiliently check barrel 114 retracts radially after the check head 112 of the snap post 119 traverses the check barrel 114, such that the end face 118 of the check barrel 114 comes into contact with the stop face 117 of the check barrel 114 of the check head 112, but the snap-fit post 119 can rotate arbitrarily within a 360 degree range within the check barrel 114.

Preferably, the snap-fit post 119 is further provided with a head portion 103, 104, which is provided with a channel 120, 121 which is a channel for fixing the anchoring end 122 of the strap 105, and/or a channel for gearing into the locking end 123 of the strap 105.

Preferably, the channel used to stop the anchoring end 122 of the strap 105 is a step square hole, while the channel used to gear into the fixing end 123 of the strap 105 is provided with a stop tongue 124. Preferably, the stop tongue 124 is provided with a stop tooth 125.

Preferably, the check barrel 114 is disposed at a central portion of the snap mount 110, which includes a base plate, the check barrel 114 is disposed in the center of the base plate, being perpendicular to the base plate. Preferably, the side wall of the check barrel 114 is provided with at least one slit along its parent line.

Preferably, a guiding sleeve or guiding rod 115 perpendicular to the base plate is symmetrically provided on both sides of the check barrel 114 with respect to the longitudinal direction of the base plate.

Preferably, there is further provided with a snap flap 111. In the center of the snap flap 111, there is provided with a central bore 126 that mates with the outer peripheral surface of a support cylinder 113 of the check barrel 114. Both sides of the snap flap 111 are symmetrically provided with a guiding rod or guiding sleeve 116 that is perpendicular to the snap flap 111. The guiding rod or guiding sleeve 116 mates with the guiding sleeve or guiding rod 115.

Preferably, the thickness of the base plate outside the guiding sleeve or guiding rod 115 is not greater than the thickness of the base plate inside between the two guiding sleeves or guiding rods 115 with respect to the longitudinal direction of the base plate. The outer diameter of one end of the check barrel 114 away from the base plate is not smaller than the outer diameter of the check barrel 114 adjacent to the other end of the base plate. The check barrel 114 is connected with the base plate through the support cylinder 113. The included angle formed between the outer side wall of the check barrel 114 and the inner side wall of the support cylinder 113 is an acute angle.

Preferably, the sum of the height of the check barrel 114 and the height of the check head 112 is not greater than the height of the support cylinder 113.

Preferably, the material of the mesh plate comprises 40-75 wt % of polycaprolactone, 18-50 wt % of filler, and 7-10 wt % of auxiliary materials. Preferably the material further comprises a coupling agent. In the mesh plate with large ventilation holes, the hollowed-out areas account for 7-70% of the total area of the mesh plate.

According to the second aspect of the present invention, there is provided a fixing support which has large ventilation holes thereon, is formed by injection molding, and is made from a shape memory material, in which a blended raw material comprises polycaprolactone, filler and auxiliary materials (preferably, with respect to compositions, the raw material comprises 40-75 wt % of polycaprolactone, 18-50 wt % of a filler, and 7-10 wt % of an auxiliary material;

preferably, the raw material further comprises a coupling agent); with the large ventilation holes, the hollowed-out areas account for 7-70% of the total area of the fixing support; and the enclosing and locking means is capable of being disassembled and capable of adjusting the locking tightness thereof.

Preferably, the filler is polypropylene and/or polyethylene; and/or, the filler is calcium carbonate and/or glass fiber.

Preferably, the coupling agent is monoalkoxy titanate; the auxiliary material is grafted polypropylene and/or grafted polyethylene; and/or, the auxiliary material is polyethylene wax, calcium stearate, stearamide, and/or vegetable oil.

Preferably, the adjustable outer fixing support is provided with a snap-fit means adjacent to the two edges parallel to longitudinal axis of the fixing support; the snap-fit means can be adhered on/inserted into the shape memory mesh plate or integrated with the shape memory mesh plate; the thickness of the snap-fit means can be approximately the same as that of the shape memory mesh plate; the enclosing and locking means can be a backstop buckle structure, a nylon adhesive tape structure, a button structure, a mortise and tenon structure, or a waistband type structure with a fixing needle and a series of receiving holes.

In accordance with the third aspect of the present invention, there is provided a method for making a fixation brace, comprising the steps of: weighing the components, respectively, according to the polycaprolactone composite formulation; mixing the weighed components to obtain a mixed material; making melt extrusion and granulation on the mixed material to obtain the polycaprolactone composite material; wherein in the melt extrusion, a first zone (rear zone) temperature is 130-140° C., a second zone (middle zone) temperature is 140-150° C., a third zone (middle zone) temperature is 150-160° C., a fourth zone (front zone) temperature is 160-170° C., an injecting nozzle temperature is 170-180° C., a residence time is 1-2 min, and a pressure is 10-20 MPa.

Preferably, the composite material is subjected to drying treatment before pre-mixing, in which the drying temperature is 30-50° C.; the materials are melted and blended at 20-80 rpm; then the cast strip is extruded, and granulation is carried out for further melt molding.

Preferably, the outer fixing support is one-time formed in an injection molding process to obtain a shape memory mesh plate with irregularly shaped large openings; and the raw material is doped with an anti-sticking agent.

Preferably, the anti-sticking agent is selected from the group consisting of polyethylene wax, calcium stearate, stearamide, and vegetable oil.

According to the fourth aspect of the present invention, there is provided a method for using an adjustable external fixation brace, characterized in that a shape memory mesh having large vents is heated at 70-80° C. for softening; stretching is performed according to the size of position of broken bone of the patient so as to suitable for putting the mesh plate on a site where the patient's bone needs to be fixed; then a cleavage formed between the two side edges of the mesh plate is connected together with a plurality of the enclosing and locking means.

In accordance with the fifth aspect of the present invention, there is provided a usage of an adjustable external fixation brace, characterized in that the adjustable external fixation brace is used for, but is not limited to, any patient's position requiring rehabilitation, i.e. hand (including fingers, palm, wrist), upper limb portions, neck, chest, waist, lower limb portions, or feet (including ankle, sole, toes).

Having disclosed concepts according to the aspects of the present inventive, it will be apparent to those skilled in the art from this disclosure that various improvements, substitutions, additions, modifications, variations, and the like can be made to the disclosed embodiments of the present invention without departing from the scope of protection as defined by the appended claims.

The invention claimed is:

1. A medical fixing brace which has large openings thereon, is reshaped from a mesh plate formed by injection molding, and is made from a shape memory material, wherein a blended raw material comprises polycaprolactone, filler and auxiliary materials; the large openings account for 7-70% of the total area of the mesh plate; and a means for enclosing and locking the fixing brace is provided to have the fixing brace disassembled and have a locking tightness of the fixing brace adjusted;
   a plurality of step holes for assembling snap-fit seats and posts are symmetrically arranged on both sides of the mesh plate adjacent to each of two transverse edges thereof and provided on both surfaces of the mesh plate, or at least one surface is provided with a plurality of step holes for assembling the snap-fit seats and posts; the thickness of the mesh plate is made thinner at the step holes; and each of the step holes is assembled with some parts of the snap-fit seats and posts;
   the snap-fit seats and posts are provided with a snap-fit seat and a snap-fit post; the snap-fit seat is disposed within the step hole provided on one surface of the mesh plate, and the snap-fit post is rotatably inserted into the snap-fit seat from the other surface of the mesh plate, and is prevented from being drawn out of the snap-fit seat;
   the snap-fit seat is provided with an elastically expandable check barrel; the snap-fit post is provided with a check head with a stop face; the check barrel resiliently retracts radially after the check head traverses the check barrel such that an end face of the check barrel comes into contact with the stop face of the check head, the snap-fit post is rotatable arbitrarily within a 360 degree range within the check barrel; or the snap-fit post is further provided with a head portion, which is provided with a channel for fixing an anchoring end of a strap, and/or a channel for gearing into a fixing end of the strap.

2. The medical fixing brace of claim 1, wherein the filler is polypropylene and/or polyethylene; and/or, the filler is calcium carbonate and/or glass fiber.

3. The medical fixing brace of claim 1, further comprising a coupling agent, wherein the coupling agent is monoalkoxy titanate; the auxiliary material is grafted polypropylene and/or grafted polyethylene; and/or, the auxiliary material is polyethylene wax, calcium stearate, stearamide, and/or vegetable oil.

4. The medical fixing brace of claim 1, wherein the fixing brace is one-time formed in an injection molding process to obtain a shape memory mesh plate with irregularly shaped large openings; and the raw material is doped with an anti-sticking agent.

5. The medical fixing brace of claim 4, wherein the anti-sticking agent is selected from the group consisting of polyethylene wax, calcium stearate, stearamide, and vegetable oil.

6. The medical fixing brace of claim 1, wherein the fixing brace is adjustable to enclose a position of a broken bone, and is provided with the plurality of snap-fit seats and posts adjacent to two edges parallel to a longitudinal axis of the fixing brace; the snap-fit seats and posts can be adhered on/inserted into the shape memory mesh plate or integrated with the shape memory mesh plate; the thickness of the snap-fit seats and posts is approximately the same as that of the shape memory mesh plate; the means for enclosing and locking the fixing brace is a backstop buckle structure, a nylon adhesive tape structure, a button structure, a mortise and tenon structure, or a waistband type structure with a fixing needle and a series of receiving holes.

7. The medical fixing brace of claim 1, wherein the channel for stopping the anchoring end of the strap is a step square hole, while the channel for gearing into the fixing end of the strap is provided with a stop tongue or a stop tooth.

8. The medical fixing brace of claim 1, wherein the check barrel is disposed at a central of a snap mount, which includes a base plate, the check barrel is disposed in the center of the base plate, being perpendicular to the base plate; or the side wall of the check barrel is provided with at least one slit along a parent line of the check barrel.

9. The medical fixing brace of claim 8, wherein a guiding sleeve or guiding rod perpendicular to the base plate is symmetrically provided on both sides of the check barrel with respect to a longitudinal direction of the base plate.

10. The medical fixing brace of claim 9, wherein the medical fixing brace is further provided with a snap flap; in the center of the snap flap, a central hole is provided to mate with an outer peripheral surface of a support cylinder of the check barrel; both sides of the snap flap are symmetrically provided with a guiding rod or guiding sleeve that is perpendicular to the snap flap; and the guiding rod or guiding sleeve mates with the guiding sleeve or guiding rod.

11. The medical fixing brace of claim 10, wherein the thickness of the base plate outside the guiding sleeve or guiding rod is not greater than the thickness of the base plate inside, between the two guiding sleeves or guiding rods with respect to the longitudinal direction of the base plate; the outer diameter of one end of the check barrel away from the base plate is not smaller than the outer diameter of the check barrel adjacent to the other end of the base plate; the check barrel is connected with the base plate through the support cylinder; and the included angle formed between the outer side wall of the check barrel and the inner side wall of the support cylinder is an acute angle.

12. The medical fixing brace of claim 10, wherein the sum of the height of the check barrel and the height of the check head is not greater than the height of the support cylinder.

13. The medical fixing brace of claim 1, wherein the material of the mesh plate comprises 40-75 wt % of polycaprolactone, 18-50 wt % of filler, and 7-10 wt % of auxiliary materials; or the material further comprises a coupling agent.

* * * * *